(12) United States Patent
Simoneau et al.

(10) Patent No.: US 6,323,202 B1
(45) Date of Patent: Nov. 27, 2001

(54) HSV PRIMASE INHIBITORS

(75) Inventors: Bruno Simoneau, Laval; Michele Liuzzi, Outremont, both of (CA); Anton Mentrup, Mainz-Kastel (DE)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/534,063

(22) Filed: Mar. 24, 2000

Related U.S. Application Data

(60) Provisional application No. 60/126,165, filed on Mar. 25, 1999.

(51) Int. Cl.⁷ .................................................. A61K 31/535
(52) U.S. Cl. .................. 514/237.5; 514/255; 514/315; 514/428; 514/616; 514/617; 544/162; 544/165; 548/562; 564/164; 564/170; 564/175; 564/176; 564/177; 564/179
(58) Field of Search .................................. 564/177, 179, 564/164, 170, 175, 176; 546/234, 226, 400; 544/162, 165; 548/567; 514/237.5, 255, 315, 428, 616, 617

(56) References Cited

U.S. PATENT DOCUMENTS

| 4,358,443 | 11/1982 | Coburn et al. |
| 5,693,827 | 12/1997 | Harrison et al. |

FOREIGN PATENT DOCUMENTS

| 793882 | 9/1968 | (CA) |
| 497816 | 5/1995 | (EP) |
| WO 96/41795 | 12/1996 | (WO) |
| WO 97/19062 | 5/1997 | (WO) |
| WO 98/34909 | 8/1998 | (WO) |

OTHER PUBLICATIONS

P.R. Andrews et al., Structure and Conformations of GABA–Transaminase Inhibitors. IV Transition State Analogues, Australian Journal of Chemistry, 1998, 493–503, (41).

Primary Examiner—Alan L. Rotman
Assistant Examiner—Raymond Covington

(74) Attorney, Agent, or Firm—Robert P. Raymond; Alan R. Stempel; Mary-Ellen M. Devlin

(57) ABSTRACT

The invention provides compounds of the formula 1 that are active against the HSV primase enzyme:

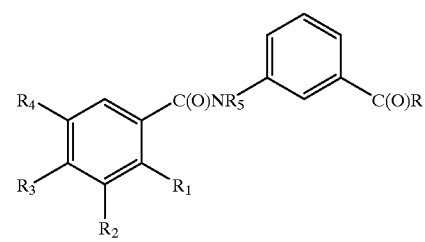

(1)

wherein $R_1$ is hydroxy or amino;

$R_2$ is hydrogen, halo, $(C_{1-4})$alkyl or $(C_{1-4})$alkoxy; $R_3$ is hydrogen, halo, $(C_{1-4})$alkyl, $(C_{1-4})$alkoxy, amino or azido; $R_4$ has the same significance as $R_2$;

$R_5$ is hydrogen or $(C_{1-4})$alkyl; and R is $(C_{1-7})$alkyl, $(C_{3-6})$cycloalkyl, {phenyl$(C_{1-7})$alkyl}, {phenyl$(C_{1-7})$alkoxy}, {{(monocyclic heterocyclo)-{$(C_{1-7})$alkoxy}}, CH(W)C(O){O-$(C_{1-4})$alkyl} wherein W is hydrogen or $(C_{1-7})$alkyl, or

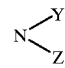

wherein Y is hydrogen or $(C_{1-7})$alkyl, and Z is $(C_{1-7})$alkyl, $(C_{3-6})$ cycloalkyl, {$(C_{3-6})$cycloalkyl}- {$(C_{1-7})$alkyl}, phenyl$(C_{1-7})$alkyl or {{(monocyclic heterocyclo)-{$(C_{1-7})$alkyl}}, or Y and Z together with the nitrogen atom to which they are attached represent, 1-pyrrolidinyl, 1-piperidinyl, 4-morpholinyl or 1-(4-methylpiperazinyl); with the provisos that (1) when R is CH(W)C(O)-{O-$(C_{1-4})$alkyl} as defined herein, then $R_5$ is hydrogen; and (2) at least one of $R_2$, $R_3$ and $R_4$ is other than hydrogen.

19 Claims, No Drawings

SEQUENCE LISTING

<160> NUMBER OF SEQ ID NOS: 1

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: template
      for helicase assay

<400> SEQUENCE: 1
cttcttcggt tccgactacc cctcccgact gcctatgatg tttatccttt g            51

HSV PRIMASE INHIBITORS

This application claims priority from U.S. provisional application 60/126,165 filed Mar. 25, 1999.

TECHNICAL FIELD OF THE INVENTION

This invention relates to methods for inhibiting herpes replication and for treating herpes infection in a mammal by inhibiting the herpes primase enzyme. In a preferred embodiment, this invention relates to compounds that inhibit the primase activity of the herpes helicase-primase enzyme. This invention also relates to pharmaceutical compositions comprising the compounds, and to methods of using and producing the compounds.

BACKGROUND OF THE INVENTION

Herpesviruses are the causative agents of a wide range of diseases suffered by humans and animals. For instance, herpes simplex viruses, types 1 and 2 (HSV-1 and HSV-2), are responsible for cold sores and genital lesions, respectively; varicella zoster virus (VZV) causes chicken pox and shingles; and the human cytomegalovirus (HCMV) is a leading cause of opportunistic infections in immunosuppressed individuals.

Herpes viruses are complex double-stranded DNA viruses that encode the enzymes that directly mediate Viral DNA replication. Seven DNA replication-associated polypeptides are required for human herpesvirus replication. Six of these seven polypeptides show a high degree of homology across all studied human herpesviruses. These six polypeptides, when expressed by the virus, include a heterodimeric DNA-dependent DNA polymerase, a monomeric single-stranded DNA binding protein, and a heterotrimeric helicase-primase complex that exhibits DNA-dependent ATPase activity, helicase activity and primase acuvity. The seventh DNA replication-associated polypeptide does not display sequence or functional conservation and is involved in the initiation of lytic viral replication.

Without the function of each of the seven herpesvirus-specific DNA replication proteins, herpesvirus chromosomal replication will not initiate or propagate. This has been demonstrated in two ways for DNA replication in HSV-1. First, temperature sensitive HSV-1 strains have been developed and the complementation groups within these strains have been mapped on a one-to-one correspondence to the seven HSV DNA replication genes. Additionally, transient replication assays that utilized recombinant DNA plasmids containing single DNA replication genes have found that the presence of each of the seven genes was required for the efficient replication of a tester plasmid containing an HSV-1 origin of DNA replication.

More recently, the DNA replication genes in other herpesviruses (i.e., Epstein-Barr virus, cytomegalovirus and varicella zoster virus) have been sequenced. These gene sequences are largely homologous to the HSV-1 DNA replication genes. Furthermore, transient replication assays containing either an Epstein-Barr virus or cytomegalovirus lytic origin of DNA replication confirmed their identity. In varicella zoster virus (the human herpesvirus most closely related to HSV-1) DNA replication genes were found to be highly homologous to HSV-1 (>50% at the amino acid level) and present at identical relative locations on the two viral chromosomes. Although no follow-up analysis on varicella zoster virus DNA replication genes has been presented to date, it is highly unlikely that differences in the varicella zoster virus and HSV-1 DNA replication programs exist.

From the above, it is clear that human DNA replication proteins are unable to substitute for the HSV-1 encoded enzymes. Otherwise, temperature-sensitive viral polypeptides would have been complemented by human counterparts and the defective viruses would have continued to grow and replicate, even at elevated temperatures. Similarly, in transient replication assays, H human proteins were capable of complementing any of the seven herpesvirus-encoded polypeptides, an absolute dependence on the presence of each of these herpesvirus DNA replicafion-specific genes would not have been observed. Therefore, inhibiting the activity of these virally-encoded proteins represents an effective way of preventing herpesviral replication.

The herpes primase enzyme plays a critical role in the herpesvirus DNA replication program. The observation that the gene encoding the herpes primase is not only essential for replication, but is also highly conserved across the range of known herpesviruses, underscores the importance of this enzyme in mediating viral chromosomal replication.

In the helicase-primase complex, two of the three polypeptides (e.g., the expression products of the UL5 and UL52 genes of HSV-1) promote catalysis of duplex DNA unwinding (helicase) and RNA primer biosynthesis (primase). The third polypeptide, encoded by the UL8 gene, appears to modulate primase activity. The assembled helicase-primase enzyme complex functions both in the initiation and propagaton stages of herpesvirus DNA replication. It is responsible for the synthesis of RNA primers necessary for the initiation of all new DNA synthesis by the herpesvirus DNA polymerase. Additionally, for DNA replication to proceed, duplex viral chromosomal DNA must first be unwound to the single-stranded replicative intermediate because the herpesvirus DNA polymerase is inactive on fully duplex DNA. The helicase-primase is also responsible for this important DNA unwinding event.

Known anti-herpes therapies have not focused on inhibiting the primase activity of the herpes helicase-primase. The most widely used anti-herpes agents to date are purine and pyrimidine nucleoside analogs, such as acyclovir and ganciclovir. These nucleoside analogues inhibit replication of viral DNA by their incorporation into a growing DNA strand. The nucleoside analogue-based inhibitors of HSV-1 growth have found only limited success and are not generally useful in treating recurring infections in the majority of patients. In addition, the infection of humans by other herpesviruses, such as varicella zoster virus or cytomegalovirus, show little or no responsiveness to nucleoside-based therapies.

The lack of broad spectrum anti-herpesvirus activity by the nucleoside-based therapies is not surprising because these compounds act by indirect biological mechanisms. Nucleoside analogues must first be activated to the nucleoside monophosphate by a virally-encoded thymidine kinase enzyme. It should be pointed out that only HSV and varicella zoster virus encode thymidine kinase enzymes. This may, in part, explain the inability to adapt nucleoside-based therapies to the treatment of other human herpesviruses. After initial phosphorylation, the nucleoside analogue monophosphate must be further phosphorylated to the triphosphate by human-encoded enzymes prior to its action. Ultimately, the triphosphorylated nucleoside analogue is incorporated into a nascent DNA chain during viral genomic replication, thereby inhibiting the elongation of that DNA chain by the herpes DNA polymerase.

The final incorporation step of the nucleosidebased therapies has been characterized as "competitive" because the herpes DNA polymerase does not display a preference for the activated nucleoside drug versus normal deoxynucleoside triphosphates. However, because the action of the DNA polymerase is not considered rate-limiting for herpesvirus DNA replication, the utility of nucleoside-derived compounds in treating herpesvirus infections is necessarily limited. Accordingly, the need for effective, safe therapeutic agents for treating herpesvirus infections continues to exist.

References disclosing N-(carbonylphenyl)benzamide derivatives include the following:

A. A. Patchett et al., Canadian patent 793,882, Sep. 3, 1968,

R. A. Coburn et al., U.S. Pat. No. 4,358,443, Nov. 9, 1982,

P. R. Andrews et al., Australian Journal of Chemistry, 1988, 41, 493,

W. A. Harrison et al., European patent application 497 816, May 17, 1995,

H. Setoi et al., PCT patent application WO 96/41795, published Dec. 27, 1996,

M. Teng et al., PCT patent application WO 97/19062, May 29, 1997,

J.-M. Bernardon, PCT patent application WO 98/34909, published Aug. 13, 1998, and W. A. Harrison et al., U.S. Pat. No. 5,693,827, Dec. 2, 1997.

SUMMARY OF THE INVENTION

In a first aspect, the invention provides compounds of the formula 1

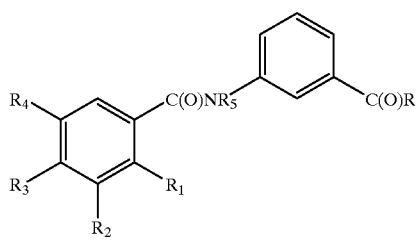

(1)

wherein $R_1$ is hydroxy or amino;

$R_2$ is hydrogen, halo, $(C_{1-4})$alkyl or $(C_{1-4})$alkoxy;

$R_3$ is hydrogen, halo, $(C_{1-4})$alkyl, $(C_{1-4})$alkoxy, amino or azido;

$R_4$ has the same significance as $R_2$;

$R_5$ is hydrogen or $(C_{1-4})$alkyl; and

R is $(C_{1-7})$alkyl, $(C_{3-6})$cycloalkyl, {phenyl$(C_{1-4})$alkyl}, {phenyl$(C_{1-7})$alkoxy}, {{(monocyclic heterocyclo)-{$(C_{1-7})$alkoxy}}, CH(W)C(O){O-$(C_{1-4})$alkyl} wherein W is hydrogen or $(C_{1-7})$alkyl, or

wherein Y is hydrogen or $(C_{1-7})$alkyl, and Z is $(C_{1-7})$ alkyl, $(C_{3-6})$cycloalkyl, {$(C_{3-6})$cycloalkyl}-{$(C_{1-7})$ alkyl}, phenyl$(C_{1-7})$alkyl or {{(monocyclic heterocyclo)-{$(C_{1-7})$alkyl}}, or Y and Z together with the nitrogen atom to which they are attached represent, 1-pyrrolidinyl, 1-piperidinyl, 4-morpholinyl or 1-(4-methylpiperazinyl);

with the provisos that (1) when R is CH(W)C(O)-{O-$(C_{1-4})$alkyl} as defined herein, then $R_5$ is hydrogen; and (2) at least one of $R_2$, $R_3$ and $R_4$ is other than hydrogen.

A preferred group of compounds is represented by formula 1 wherein $R_1$ is hydroxy or amino, $R_2$ is hydrogen or halo, $R_3$ is hydrogen, halo, $(C_{1-4})$alkyl, $(C_{1-4})$alkoxy, amino or azido, $R_4$ is hydrogen or halo, $R_5$ is hydrogen or $(C_{1-4})$alkyl, and R is $(C_{1-7})$alkyl, $(C_{3-6})$cycloalkyl, phenyl{$(C_{1-7})$alkyl}, {phenyl$(C_{1-7})$alkoxy}, {(monocylic heterocyclo){$(C_{1-7})$alkoxy)}}, CH(W)C(O)-{O-$(C_{1-4})$alkyl} wherein W is hydrogen or $(C_{1-7})$alkyl, or

wherein Y is hydrogen and Z is $(C_{1-7})$alkyl, $(C_{3-6})$ cycloalkyl, {$(C_{3-6})$cycloalkyl}-{$(C_{1-7})$alkyl}, phenyl{$(C_{1-7})$alkyl}, or {(monocyclic heterocyclo)-{$(C_{1-7})$ alkyl}, or Y and Z together with the nitrogen atom to which they are attached represent 1-pyrrolidinyl, 1-piperidinyl, 4-morpholinyl or 1-(4-methylpiperazinyl).

A more preferred group of compounds is represented by formula 1 wherein $R_1$ is hydroxy or amino, $R_2$ is hydrogen or chloro, $R_3$ is hydrogen, chloro, methyl, methoxy, amino or azido, $R_4$ is hydrogen, chloro or iodo, $R_5$ is hydrogen or methyl, and R is methyl, ethyl, propyl, butyl, pentyl, hexyl, cyclopentyl, cyclohexyl, phenylmethyl, 2-phenylethyl, phenylmethoxy, 2-phenylethoxy, 2-, 3- or 4-pyridinylmethoxy, 2-(2-, 3- or 4-pyridinyl)ethoxy, $CH_2C(O)\{O-\{(C_{1-4})alkyl\}\}$, $CH\{(C_{1-7})alkyl\}C(O)\{OC_{1-4})alkyl\}$, $(C_{1-7})$alkylamino, cyclopentylamino, cyclohexylamino, (cyclohexylmethyl)amino, (2-cyclohexylethyl)amino, (phenylmethyl)amino, (2-phenylethyl)amino, 2-(3- or (4-pyridylmethyl) amino or 2-(2-, (3- or (4-pyridylethyl)amino.

A most preferred group of compounds is represented by formula 1 wherein $R_1$ is hydroxy, $R_2$ is hydrogen, $R_3$ is methyl, methoxy, amino or azido, $R_4$ is hydrogen, chloro or iodo, $R_5$ is hydrogen, and R is pentyl, hexyl, cyclohexyl, phenylmethyl, 2-phenylethyl, phenylmethoxy, 2-, 3- or 4-pyridinylmethoxy, $CH_2C(O)OCH_2CH_3$, $CH(CH_2CH_2CH_2CH_3)C(O)OCH_2CH_3$, ethylamino, propylamino, butylamino, cyclohexylamino, (cyclohexylmethyl)amino, (2-cyclohexylethyl)amino, (phenylmethyl)amino, (2-phenylethyl)amino, or (2-, (3- or (4-pyridyl-methyl)amino, or 2-(2-, (3, or (4-pyridinylethyl)amino.

A further objective of this invention is to provide compounds useful in the methods of this invention and for pharmaceutical compositions comprising those compounds.

Another objective of this invention is to provide processes for preparing the compounds of this invention.

Still a further objective of this invention is to provide pharmaceutical compositions containing the compounds of this invention and methods for treating herpes infection in a mammal using those pharmaceutical compositions.

DETAILED DESCRIPTION OF THE INVENTION

The invention described herein overcomes the limitations associated with known anti-herpes agents, by providing non-nucleoside-based inhibitors of herpes replication, i.e. N-(3-carbonylphenyl)benzamide derivatives. Without being bound to theory, it is believed that the compounds of the invention act directly in interfering with the likely rate-limiting process in herpesvirus DNA replication: the action of the herpes primase enzyme. Furthermore, since the herpesvirus primase enzyme is conserved across the human herpesviruses, compounds of this invention are effective against other herpesviruses, including HSV and varicella zoster virus, and also against nucleoside-nonresponsive and nucleoside-resistant herpes infections.

As used herein, the following definitions apply unless otherwise noted:

The term "herpes" as used herein refers to a herpes virus while encodes the herpes primase of HSV-1, and to those herpesviruses that encode a herpes primase homologous to the herpes primase of HSV-1. The herpes family of viruses includes, but is not limited to, HSV-1, HSV-2, varicella zoster virus and Epstein-Barr virus.

The term "halo" as used herein means a halo radical selected from bromo, chloro, fluoro or iodo.

The term "$(C_{1-4})$alkyl" as used herein, either alone or in combination with another radical, means alkyl radicals containing from one to four carbon atoms and includes methyl, ethyl, propyl and 1-methylethyl, butyl, 1-methylpropyl, 2-methylpropyl and 1,1-dimethylethyl.

The term "$(C_{1-7})$alkyl" as used herein means straight and branched chain alkyl radicals containing from one to seven carbon atoms and includes ethyl, butyl, 1-methylpropyl, 1-ethylpropyl, 2,2-dimethylpropyl, 1-ethylbutyl, 2-ethyl-2-methylbutyl, 2-ethylbutyl, 1-propylbutyl, 2-propylbutyl and the like.

The term "$(C_{3-6})$cycloalkyl" as used herein, either alone or in combination with another radical, means saturated cyclic hydrocarbon radicals containing from three to six carbon atoms and includes cyclopropyl, cyclobutyl, cyclopentyl and cyclohexyl.

The term "$(C_{1-4})$alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "$(C_{1-7})$alkoxy" as used herein, either alone or in combination with another radical, means straight chain alkoxy radicals containing one to seven carbon atoms and branched chain aloxy radicals containing from three to seven carbon atoms and includes the alkoxy group noted in the preceding paragraph, as well as pentyloxy, hexyloxy, 1-propylbutoxy and the like.

The term "amino" as used herein means an amino radical of formula —$NH_2$. The term "$(C_{1-7})$alkylamino" as used herein means an alkylamino radicals containing one to seven carbon atoms and includes methylamino, propylamino, (1-methylethyl)amino and (2-methylbutyl)amino.

The term "monocyclic heterocyclo" as used herein means a monovalent radical derived by removal of a hydrogen from a five- or six-membered saturated or unsaturated heterocycle; said five-membered heterocycle may contain up to four nitrogen atoms (for example tetrazolyl), or said five- or six-membered heterocycle may contain from one to three heteroatoms selected from nitrogen, oxygen and sulfur. Optionally, the heterocycle may bear one or two substituents; for example, N-oxido, $(C_{1-4})$alkyl, phenyl$(C_{1-4})$alkyl, $(C_{1-4})$alkoxy, halo, amino or $(C_{1-7})$alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, morpholine, pyridine and pyridine N-oxide.

The term "pharmaceutically acceptable carrir" or "veterinarily acceptable carrier" as used herein means a non-toxic, generally inert vehicle for the active ingredient which does not adversely affect the ingredient.

The term "effective amount" means an antiviral amount of the antiviral agent, i.e. an amount of the agent sufficient to be effective against the virus in vivo.

Processes for Preparing the Compounds

The compounds of this invention can be prepared by a variety of conventional processes. Description of some such processes are found in standard textbooks such as "Annual Reports In Organic Synthesis—1996", P. M. Weintraub et al., Eds., Academic Press, Inc., San Diego, Calif., USA, 1996 (and the preceding annual reports), "Vogel's Textbook of Practical Organic Chemistry", $5^{th}$ Ed., B. S. Furniss et al., Eds., Longman Group Umited, Essex, UK, 1989, and "Comprehensive Organic Synthesis", B. M. Trost and I. Fleming, Eds., Pergamon Press, Oxford, UK, 1991, Volumes 1 to 8.

A process for preparing a compound of formula 1 wherein R is $(C_{1-7})$alkyl, $(C_{3-6})$cycloalkyl, phenyl or phenyl$\{(C_{1-7})$alkyl is represented by Scheme 1 wherein $R_A$ is $(C_{1-7})$alkyl or phenyl$\{(C_{1-7})$alkyl$\}$, $R_{1A}$ is $(C_{1-4})$alkoxy or nitro, $R_2$ and $R_4$ each is hydrogen, halo, $(C_{1-4})$alkyl or $(C_{1-4})$alkoxy, $R_{3A}$ is hydrogen, halo, $(C_{1-4})$alkyl, $(C_{1-4})$alkyl, nitro or azido and $R_B$ is $(C_{1-7})$alkyl, $(C_{3-6})$cycloalkyl, phenyl or phenyl$\{(C_{1-7})$alkyl).

Scheme 1

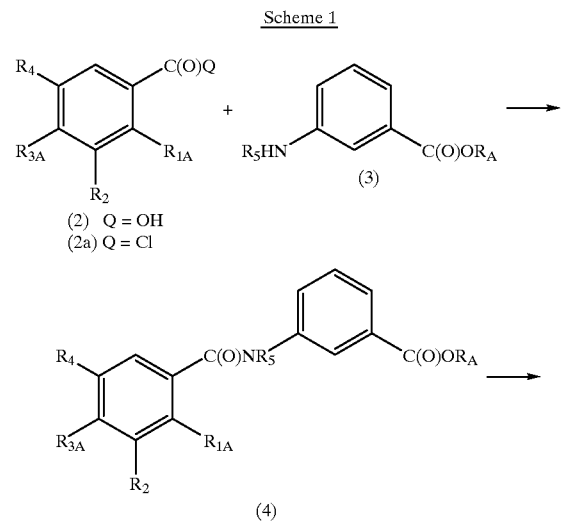

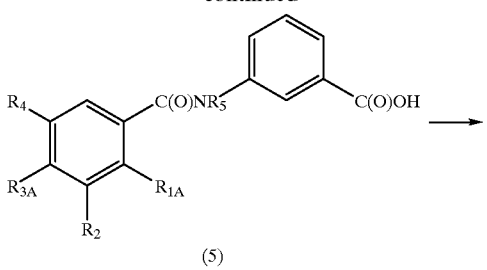

(5)

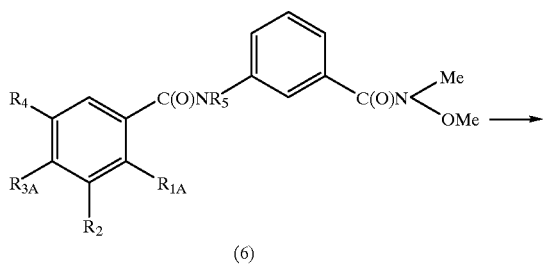

(6)

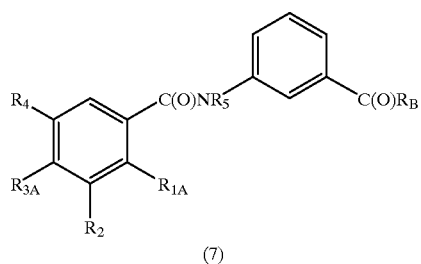

(7)

Corresponding compound of formula 1 wherein R is $(C_{1-7})$alkyl, $(C_{3-6})$cycloalkyl, phenyl or {phenyl$(C_{1-7})$alkyl}, $R_1$ is hydroxy or amino, $R_3$ is hydrogen, halo, $(C_{1-4})$alkyl, $(C_{1-4})$alkoxy, amino or azido.

With reference to Scheme 1, a substituted benzoic acid of formula 2 is onverted to its corresponding acid chloride 2a and the latter is reacted with an aminobenzoate of formula 3, in the presence of an acid scavanger such as triethylamine, to yield a benzoylaminobenzoate of formula 4. The latter compound is subjected to a basic hydrolyzing agent (e.g. aqueous sodium hydroxide) to yield the corresponding benzoic acid derivative of formula 5. Thereafter, the benzoic acid derivative 5 is coupled with N,O-dimethylhydroxylamine in the presence of a coupling agent to obtain the corresponding N-methoxy-N-methylbenzamide of formula 6. In turn, the N-methoxy-N-methylbenzamide is reacted with either an appropriate Grignard reagent of formula $R_B$—Mg-(halo) or organolithium reagent of formula $R_B$-Li wherein $R_B$ is $(C_{1-7})$alkyl, $(C_{3-6})$cycloalkyl, phenyl or phenyl{$(C_{1-7})$alkyl}, according to the acylating method of S. Nahm and S. M. Weinreb, Tetrahedron Letters, 1981, 22, 3815, to give the corresponding benzoylaminobenzoyl derivative of formula 7.

Subsequent ether cleavage of the alkoxy of $R_{1A}$, if present, with aluminium chloride in a inert solvent such as methylene dichloride, benzene or carbon tetrachloride; or reduction of the nitro group of $R_{1A}$ and/or $R_{3A}$ if present with an appropriate reducing agent, preferably triethylsilane in the presence of Wilkinson's catalyst, i.e. $RhCl(PPh_3)_3$, described by H. R. Brinkman, Synthetic Communications, 1996, 26, 973, in an inert aromic solvent such as benzene or toluene; transforms the benzoylaminobenzoyl derivative of formula 7 into the corresponding desired compound of formula 1 wherein R is $(C_{1-7})$alkyl, $(C_{1-6})$cycloalkyl, phenyl or phenyl{$(C_{1-7})$alkyl} and $R_1$ and $R_3$ are as defined herein.

The coupling of the benzoic acid derivative of formula 5 and N,O-dimethylhydroxylamine is effected by the classical dehydrative coupling of a free carboxyl of one reactant with the free amino group of the other reactant in the presence of coupling agent to form a linking amide bond. Description of such coupling agents are found in general textbooks on peptide chemistry; for example, M. Bodanszky, "Peptide Chemistry", 2nd rev ed, Springer-Verlag, Berlin, Germany, 1993. Examples of suitable coupling agents are N,N'-dicyclohexyl-carbodiimide, 1-hydroxybenzotriazole in the presence of N,N'-dicyclohexylcarbodiimide or Nethyl-N'-{(3-dimethylamino)propyl}carbodiimide. A very practical and useful coupling agent is the commercially available (benzotriazol-1-yloxy)tri-(dimethylamino)phosphonium hexafluorophosphate, either by itself or in the presence of 1-hydroxybenzotriazole. Still another very practical and useful coupling agent is commercially available 2-(1H-benzotriazol-1-yl)-N,N,N',N'-tetramethyl-uronium tetrafluoroborate.

The coupling reaction is conducted in an inert solvent, e.g. dichloromethane, dimethylformamide, tetrahydrofuran or acetonitrile. A base, such as a tertiary amine, e.g. diisopropylethylamine or N-methylmorpholine, may be added. The reaction temperature usually ranges between 0° and 50° and the reaction time usually ranges between 15 min and 24 h.

Alternatively, the N-methoxy-N-methyl benzamide of formula 6 wherein $R_5$ is hydrogen can be readily N-alkylated (at the secondary amide) by conventional methods to give the corresponding N-methoxy-N-methylamide of formula 6 wherein $R_5$ is $(C_{1-7})$alkyl.

The latter N-alkylated amido derivative can then be transformed to a corresponding compound of formula 1 as described hereinbefore via the step sequence represented by formula 6→7→1.

A process for preparing a compound of formula 1 wherein R is hydroxy and $R_1$ is hydroxy, involves cleavage of the ether with aluminum chloride of the appropriate benzoic acid of formula 5 wherein $R_{1A}$ is $(C_{1-4})$alkoxy, in the manner described previously, to obtain the corresponding compound of formula 1 wherein R is hydroxy and $R_1$ is hydroxy.

A compound of formula 1 wherein R is $(C_{1-7})$alkoxy or phenyl{$(C_{1-7})$alkoxy} and $R_1$ and/or $R_3$ is amino can be prepared by reducing the corresponding benzoylamino benzoate of formula 4 wherein $R_1$ and/or $R_3$ is nitro, according to the nitro group reduction method described previously, to obtain the corresponding compound of formula 1 wherein R is $(C_{1-7})$alkoxy or phenyl{$(C_{1-7})$alkoxy} and $R_1$ andlor $R_3$ is amino.

A process for preparing a compound of formula 1 wherein R is CH(W)C(O){O-$(C_{1-4})$alkyl} wherein W is hydrogen or $(C_{1-4})$alkyl can be represented by Scheme 2 wherein $W_A$ is $(C_{1-4})$alkyl $R_C$ is $(C_{1-4})$alkoxy and $R_{1A}$, $R_2$, $R_{3A}$ and $R_4$ are as defined herein.

Scheme 2

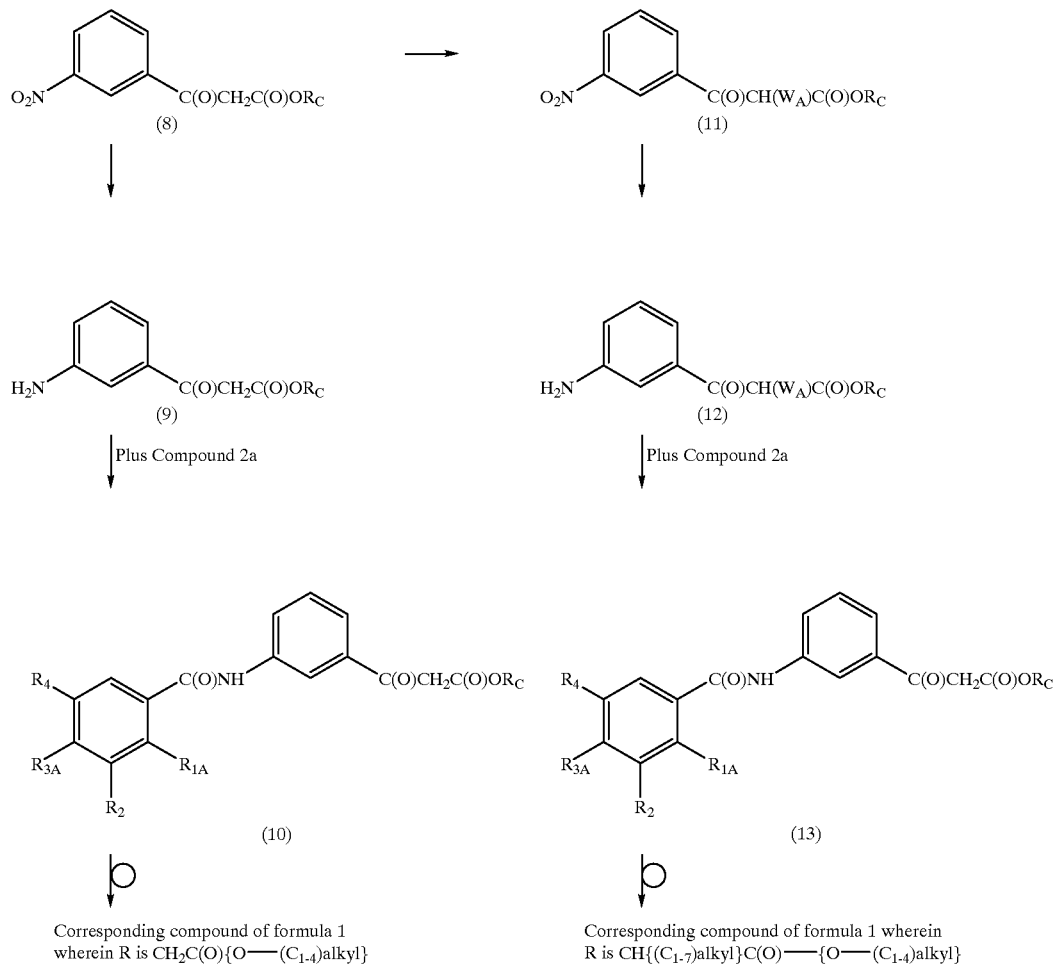

With reference to Scheme 2, the nitro-o-ketoester of formula 8 is subjected to catalytic hydrogenation (e.g. $H_2$ in the presence of Pd/tBaSO$_4$) to afford the amino-β-ketoacid of formula 9 which in turn is reacted with the acid chloride 2a in the presence of an acid scavanger, e.g. triethylamine, to yield the β-ketoester of formula 10.

Thereafter, with reference to the latter β-ketoester, the ether cleavage of the $R_{1A}$ ($C_{1-4}$)alkoxy group, if present, or the reduction of the $R_{1A}$ and/or $R_{3A}$ nitro group, if present, in the manner described above for such cleavages and reductions affords the desired compound of formula 1 wherein R is $CH_2C(O)(O$-$(C_{1-4})$alkyl) and $R_1$ is hydroxy or amino respectively.

Likewise, following the route illustrated by the compound sequence of 8→11(via C-alkylation) →12→13→corresponding compounds of formula 1, a desired compound of formula 1 wherein R is CH{($C_{1-7}$) alkyl}C(O){O-($C_{1-4}$)alkyl} and $R_1$ is hydroxy or amino can be obtained.

A variation of the previous Scheme for obtaining a compound of formula 1 wherein R is CH{($C_{1-7}$)alkyl}C(O) {O-($C_{1-4}$)alkyl} and $R_1$ is hydroxy is illustrated in Scheme 3:

Scheme 3

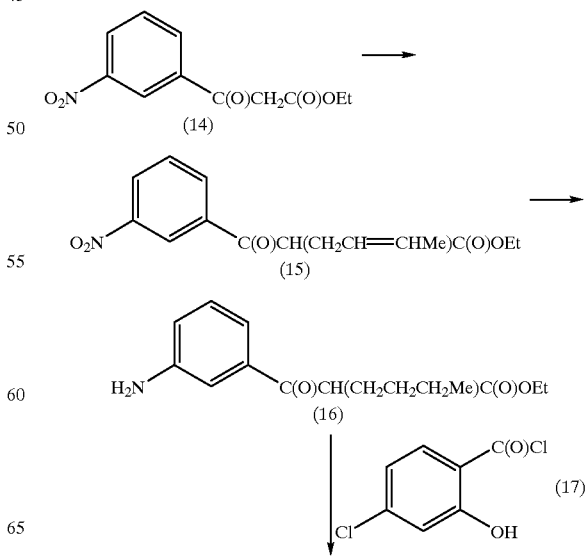

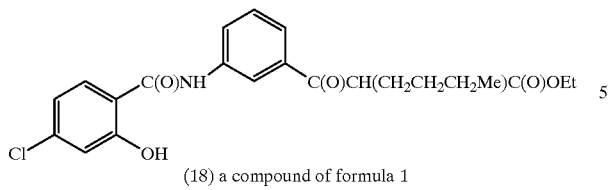

(18) a compound of formula 1

With reference to Scheme 3, the key steps are (a) the alkylation of β-ketoester 14 with 1-bromo-2-butene in the presence of sodium hydride, (b) the reduction of the nitro group and side chain double bond of the intermediate 15, and (c) the coupling of intermediate 16 with the salicylic acid derivative 17 having an unprotected (free) hydroxyl. This variation is described in detail in the experimental hereinafter. Also, noteworthy at this point is that treatment of compound 18 with lithium hydroxide, followed by acid hydrolysis, yields the compound of formula 1 in which R is pentyl, $R_1$ is hydroxy, $R_2$ and $R_4$ each is hydrogen and $R_3$ is chloro. See the experimental hereinafter.

A process for preparing a compound of formula 1 wherein R is

wherein Y is hydrogen or $(C_{1-7})$alkyl and Z is $(C_{1-7})$alkyl, $(C_{1-6})$cycloalkyl, {$(C_{3-4})$cycloalkyl} {$(C_{1-7})$alkyl}, phenyl$(C_{1-7})$alkyl or {(monocyclic heterocyclo)alkyl}, or Y and Z together with the nitrogen atom to which they are attached represent 1-pyrrolidinyl, 1-piperidinyl, 4-morpholinyl or 1-(4-methylpiperazinyl); can be represented by Scheme 4, wherein

$R_{1A}$, $R_2$, $R_{3A}$ and $R_4$ are as defined herein.

Scheme 4

(5) ⟶

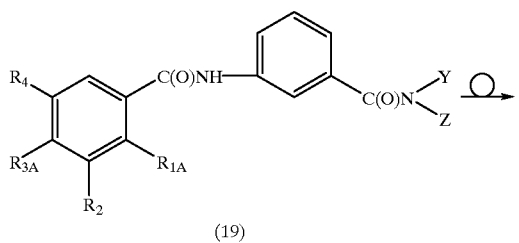

(19)

Corresponding compound of formula 1 wherein R is

wherein Y and Z are as defined herein.

According to Scheme 4, the benzoic acid derivative of formula 5 is reacted with the appropriate amine of formula

wherein Y and Z are as defined herein in the presence of a coupling agent to give the corresponding benzoylaminobenzamide of formula 19 Subsequently, for a compound of formula 19 having a $(C_{1-4})$alkoxy group at $R_{1A}$, the compound is subjected to the previously noted ether cleavage conditions (i.e. aluminium chloride in an inert solvent at room temperature) a to give the corresponding compound of formula 1 wherein R is

as defined herein and $R_1$ is hydroxy; or for a compound of formula 19 having a nitro group at $R_{1A}$, and/or $R_{3A}$, the compound is subjected to the previously described nitro reduction method, i.e. with triethylsilane and $RhCl(PPh_3)_3$, to give the corresponding compound of formula 1 wherein R is

as defined herein and $R_1$ is amino and $R_3$ is as defined herein

The starting materials for the preceding processes are known or can be prepared readily from known compounds. A number of the substituted benzoic acids of formula 2 and the aminobenzoates of formula 3 (or their corresponding acids) are available from the Aldrich Chemical CO., Milwaukee, Wis., USA.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by modifications known to those skilled in the art, e.g. by appropriate protection of interfering groups, by changing to alternative reagents, by modification of reaction conditions, or by modification illustrated in the examples herein such as preparing compounds of formula 1 wherein $R_3$ is amino by using appropriate intermediates wherein $R_{3A}$ is nitro and reducing the nitro group to finally obtain the corresponding compound of formula 1 wherein $R_3$ is amino.

If desired, compounds of formula 1 having a basic nitrogen atom can be obtained in the form of acid addition salts. Such salts can be considered as biological equivalents of the compounds of formula 1. For therapeutic applications, it is preferred to use pharmacuetically acceptable salts.

Examples of such salts are those formed with hydrochloric acid, sulfuric acid, phosphoric acid, formic acid, acetic acid or citric acid.

Antiherres Activity

The antiviral activity of the compounds of formula 1 can be demonstrated by biochemical, microbiological and biological procedures showing the inhibitory effect of the compounds on the replication of herpes simplex viruses, types 1 and 2 (HSV-1 and HSV-2), as well as acyclovir-resistant herpes simplex viruses and ganciclovir-resistant cytomegaloviruses.

A biochemical procedure for demonstrating antiherpes activity for compounds of formula 1 is described in the examples hereinafter. This particular assay is based on the evaluation of the ability of the test compound to inhibit HSV-1 primase, an essential enzyme for viral DNA replication.

Methods for demonstrating the inhibitory effect of the compounds of formula 1 on herpes viral replication involving in vitro and cell culture techniques are described in the examples.

The therapeutic effect of the compounds of formula 1 can be demonstrated in laboratory animals, for instance, the hairless mouse model for the topical treatment of cutaneous HSV-1 infections, P. H. Lee et al., International Journal of Pharmaceutics, 1993, 93, 139; the (HSV-2)-induced genitalis mouse model, R. W. Sidewell et al., Chemotherapy, 1990, 36, 58; and BALB/C mouse model infected with murine cytomegalovirus, D. L. Barnard et al., Antiviral Res., 1993, 22, 77, and J. Neyts et al., Journal of Medical Virology, 1992, 37, 67.

When a compound of formula 1, or one of its therapeutically acceptable acid addition salts, is employed as an antiviral agent, it is administered orally, topically or systemically to warm-blooded animals, e.g. humans, pigs or horses, in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier. For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula 1 is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", 19th ed., Mack Publishing Company, Easton, Penn, 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula 1 is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

With reference to topical application, the compound of formula 1 is administered topically in a suitable formulation to the infected area of the body e.g. the skin, the eye, the genitalia or part of the oral cavity, in an amount sufficient to cover the infected area. The treatment should be repeated, for example, every four to six hours until lesions heal.

For ocular administration, the compound of formula 1 is administered either topically or intraocularly (injection or implant) in a suitable preparation. For example, an implant containing the compound in a suitable formulation can be surgically placed in the posterior segment of the eye through a small incision.

With reference to systemic administration, the compound of formula 1 is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

Although the formulations disclosed hereinabove are indicated to be effective and relatively safe medications for treating herpes viral infections, the possible concurrent administration of these formulations with other antiviral medications or agents to obtain beneficial results also included. Such other antiviral medications or agents include the antiviral nucleosides, for example, acyclovir, penciclovir, famciclovir, valacyclovir and ganciclovir, and antiviral surface active agents or antiviral interferons such as those disclosed by S. S. Asculai and F. Rapp in U.S. Pat. No. 4,507,281, Mar. 26, 1985.

The following examples further illustrate and teach this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts ($\delta$) are reported in parts per million. Abbreviations or symbols used in the examples include ATP: adenosine triphosphate; Bu: butyl; i-Pr$_2$NEt: diisopropylethylamine; DMF: dimethyl-formamide; DMSO: dimethylsulphoxide; Et: ethyl; EtOAc: ethyl acetate; Et$_2$O: diethyl ether; Et$_3$N: triethylamine; ESI/MS: electro spray ionization mass spectrometry; mAb: monoclonal antibody; Me: methyl; MeOH: methanol; PFU: plaque forming units; Ph: phenyl; Pr: propyl; TBTU: 2-(1H-benzotriazol-1-yl)-N,N,N'N'-tetramethyluronium tetrafluoroborate; THF: tetrahydrofuran.

EXAMPLES

Example 1

N-Butyl-N-methyl-3-{(4-chloro-2-hydroxybenzoyl) amino)benzamide (1:R$_1$=OH, R$_2$, R$_4$ and R$_5$=H, R$_3$=Cl and R=N(Me)Bu)

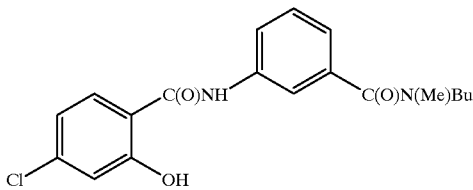

(a) Ethyl 3-{(4-chloro-2-methoxybenzoyl)amino}benzoate (4: $R_{1A}$=OMe, $R_2$ and $R_4$=H, $R_{3A}$=Cl, $R_5$=H and $R_A$=Et)

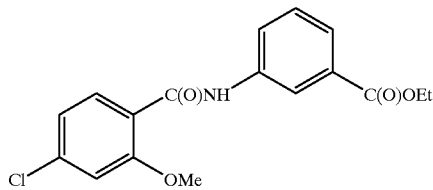

A suspension of 4-chloro-2-methoxybenzoic acid (10.0 g, 53.6 mmol), oxalyl chloride (8.84 g, 69.7 mmol) and DMF (50 μL) in $CH_2Cl_2$ (107 mL) was stirred at 25° for 2 h. The resulting clear solution was concentrated under reduced pressure. To the residual, crude acyl chloride in $CH_2Cl_2$ (107 mL) were added ethyl 3aminobenzoate (8.85 g, 53.6 mmol) and $Et_3N$ (10.8 g, 107 mmol) over 5 min at 25°. The mixture was stirred at 25° for 24 h. The resulting suspension was diluted with EtOAc (350 mL) and the resulting solution was successively washed with aqueous 1 N HCl (2×150 mL), aqueous saturated $NaHCO_3$ (2×150 mL) and brine (150 mL). The organic layer was dried ($MgSO_4$), filtered and concentrated under reduced pressure to give the desired benzoylaminobenzoate of formula 4 (17.4 g, 97% yield) as a beige solid:

$^1$H NMR (DMSO-$d_6$) δ 810.31 (s, 1H), 8.40 (broad s, 1H), 7.94 (broad d, J=7.9 Hz, 1H), 7.69 (dt, J=7.9, 1.2 Hz, 1H), 7.62 (d, J=8.2 Hz, 1H), 7.49 (t, J=7.9 Hz, 1H), 7.28 (d, J=1.9 Hz, 1H), 7.13 (dd, J=8.2, 1.9 Hz, 1H), 4.33 (q, J=7.0 Hz, 2H), 3.92 (s, 3H), 1.33 (t, J=7.0 Hz, 3H).

(b) 3-{(4-Chloro-2-methoxybenzoyl)amino}benzoic acid (5: $R_{1A}$=OMe, $R_2$ and $R_4$=H, $R_{3A}$=Cl and $R_5$=H)

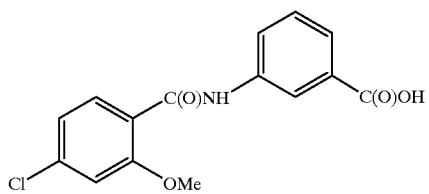

A solution of ethyl 3-{(4-chloro-2-methoxybenzoyl)amino}benzoate (12.2 g, 36.5 mmol), aqueous 1 N NaOH (55 mL, 55 mmol) in THF (75 mL) and MeOH (50 mL) was stirred at 25° for 6 h. Water (50 mL) was added and most of the THF/MeOH solvent was removed under reduced pressure. Water (100 mL) and $Et_2O$ (50 mL) were added and the phases were separated. The aqueous layer was rendered acidic (pH<2) by addition of aqueous 1 N HCl and EtOAc (300 mL) was added. The insoluble benzoic acid derivative of formula 5 was collected by filtration. The organic phase of the filtrate was concentrated under reduced pressure. The residue was dissolved in THF (40 mL) and poured into water (300 mL). The resulting suspension was filtered to give an additional portion of the benzoic acid derivative (total of 10.4 g, 93% yield for 2 fractions):

$^1$H NMR (DMSO-$d_6$) δ 11.60 (broad s, 1H), 10.27 (s, 1H), 8.37 (broad s, 1H), 7.91 (broad d, J=7.9 Hz, 1H), 7.67 (dt, J=7.9, 1.3 Hz, 1H), 7.63 (d, J=8.3 Hz, 1H), 7.46 (t, J=7.9 Hz, 1H), 7.28 (d, J=1.9 Hz, 1H), 7.13 (dd, J=8.3, 1.9 Hz, 1H), 3.92 (s, 3H).

(c) N-Butyl-N-methyl-3-{(4-chloro-2-methoxybenzonyl)amino}benzamide (7: $R_{1A}$=OMe, $R_2$, $R_4$ and $R_5$=H, $R_{3A}$=Cl and $R_B$=N(Me)Bu)

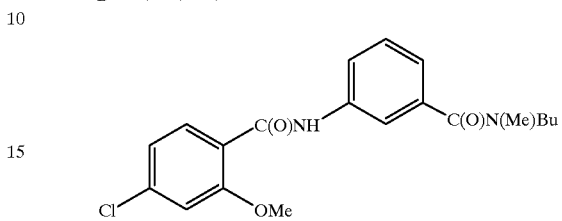

To a solution of 3-{(4-chloro-2-methoxybenzoyl)amino}benzoic acid (0.30 g, 0.98 mmol), N-butyl-N-methylamine (103 mg, 1.18 mmol) and i-$Pr_2$NEt (380 mg, 2.94 mmol) in DMF (2.0 mL) at 25° was added TBTU (315 mg, 0.98 mmol). The mixture was stirred at 25° for 1.5 h. The mixture was diluted with EtOAc (80 mL). The resulting solution was washed with aqueous 1 N HCl (2×30 mL), aqueous saturated $NaHCO_3$ (2×30 mL), water (30 mL) and brine (30 mL), dried ($MgSO_4$), filtered and concentrated under reduced pressure to give the desired benzoylaminobenzoyl derivative of formula 7 (354 mg, 96% yield) as a yellowish oil-foam:

$^1$H NMR (DMSO-$d_6$) δ.(1:1 mixture of rotamers) 10.20 (s, 1H), 7.77 (s, 1H), 7.72 (d, J=7.8 Hz, 1H), 7.63 (d, J=8.3 Hz, 1H), 7.39 (t, J=7.8 Hz, 1H), 7.28 (d, J=1.9 Hz, 1H), 7.13 (dd, J=8.3, 1.9 Hz, 1H), 7.03–7.09 (m, 1H), 3.92 (s, 3H), 3.44, 3.19 (2 broad s, 2H), 2.94, 2.88 (2 broad s, 3H), 1.62–1.45 (m, 2H), 1.40–1.27, 1.17–1.05 (2m, 2H), 0.99–0.88, 0.81–0.71 (2m, 3H).

(d) N-Butyl-N-methyl-3{(4-chloro-2-hydroxybenzoyl)amino}benzamide (the title compound of formula 1 of this example)

$AlCl_3$ (307 mg, 2.30 mmol) was added to a solution of N-butyl-N-methyl-3-{(4-chloro-2-methoxybenzoyl)amino}benzamide (345 mg, 0.92 mmol) in $CH_2Cl_2$ (3.7 mL) at 25°. The mixture was kept at 25° for 17 h. The mixture then was partitioned between EtOAc (75 mL) and aqueous 1 N HCl (50 mL). The organic layer was dried ($MgSO_4$), filtered and concentrated under reduced pressure. The residue was purified by flash chromatography (10–40μ silica gel, EtOAc:hexane, 1:1) to give the title compound (272 mg, 82% yield) as a white foam:

$^1$H NMR (DMSO-$d_6$) δ (1:1 mixture of rotamers) 11.97 (s, 1H), 10.43 (s, 1H), 7.92 (d, J=8.9 Hz, 1H), 7.79–7.74 (m, 1H), 7.74–7.67 (m, 1H), 7.42 (t, J=7.8 Hz, 1H), 7.14–7.09 (m, 1H), 7.05–7.03 (m, 2H), 3.50–3.40, 3.26–3.15 (2m, 2H), 3.30 (s, 3H), 2.95, 2.89 (2s, 3H), 1.62–1.44 (m, 2H), 1.40–1.04 (m, 2H), 1.00–0.89, 0.81–0.69 (2m, 3H); MS (ESI) m/z 361/363 (MH)$^+$.

Example 2

4-Chloro-2-hydroxy-N-{3-(1-oxohexyl)phenyl}benzamide (1: $R_1$=OH, $R_2$, $R_4$ and $R_5$=H, $R_{3A}$=Cl and R=NH—$(CH_2)_4$Me)

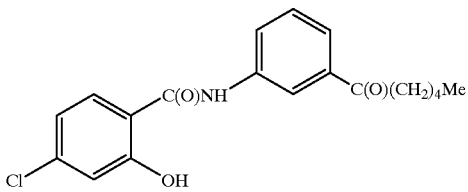

(a) 3-{(4-Chloro-2-methoxybenzoyl)amino}-N-methoxy-N-methylbenzamide (6: $R_{1A}$=OMe, $R_2$, $R_4$ and $R_5$=H, and $R_{3A}$=Cl)

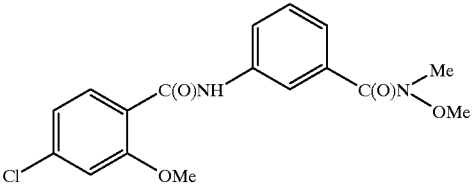

TBTU (4.73 g, 14.7 mmol) was added to a solution of 3-{(4-chloro-2-methoxybenzoyl)amino}benzoic acid (4.50 g, 14.7 mmol), N,O-dimethylhydroxylamine hydrochloride (1.72 g, 17.7 mmol) and i-$Pr_2$NEt (7.60 g, 58.9 mmol) in DMF (29 mL) at 25°. The reaction mixture was stirred at 25° for 2.5 h. The mixture was diluted with EtOAc (200 mL). The resulting solution was successively washed with aqueous 1 N HCl (2×75 mL), water (2×75 mL), aqueous saturated $NaHCO_3$ (2×75 mL) and brine (75 mL), then dried ($MgSO_4$), filtered and concentrated under reduced pressure to give the corresponding N-methoxy-N-methylbenzamide of formula 6 (4.32 g, 84% yield) as a white solid:

$^1$H NMR (DMSO-$d_6$) δ 8 10.23 (s, 1H), 7.99 (broad s, 1H), 7.79 (broad d, J=7.9 Hz, 1H), 7.63 (d, J=8.2 Hz, 1H), 7.41 (t, J=7.9 Hz, 1H), 7.29 (dt, J=7.9, 1.3 Hz, 1H), 7.28 (d, J=1.9 Hz, 1H), 7.13 (dd, J=8.2 Hz, 1.9 Hz, 1H), 3.92 (s, 3H), 3.57 (s, 3H), 3.26 (s, 3H).

(b) 4-Chloro-2-hydroxy-N-{2-(1-oxohexyl)phenyl}benzamide (the title compound of formula 1 of this example)

A 2.0 M solution of rpentylmagnesium bromide in $Et_2O$ (12.1 mL, 24.2 mmol) was added over 5 min to a solution of 3-{(4-chloro-2-methoxybenzoyl)amino)}-N-methoxy-N-methylbenzamide (1.69 g, 4.84 mmol) in THF (48 mL) at 25°. The mixture was stirred at 25° for 1 h and aqueous 1 N HCl (15 mL) was added. The mixture was partitioned between EtOAc (200 mL) and aqueous 1 N HCl (50 mL). The organic layer was successively washed with water (50 mL) and brine (50 mL), then dried ($MgSO_4$), filtered and concentrated under reduced pressure. The residue was dissolved in $CH_2Cl_2$ (19 mL) and $AlCl_3$ (1.61 g, 12.1 mmol) was added to the solution at 25°. After 2 h, a second portion of $AlCl_3$ (1.61 g, 12.1 mmol) was added to the mixture. The reaction mixture was stirred an additional 2.5 h before aqueous 1 N HCl (25 mL) was added. The mixture was partitioned between EtOAc (250 mL) and aqueous 1 N HCl (50 mL). The organic layer was washed with brine (50 mL), dried ($MgSO_4$) and concentrated under reduced pressure. The residue was purified by flash chromatography (10–40μ silica gel, hexane:EtOAc, 6:1) to afford the title compound (1.05 g, 63% yield) as a beige solid:

$^1$H NMR (DMSO-$d_6$) δ 11.98 (s, 1H), 10.53 (s, 1H), 8.29 (broad s, 1H), 7.96 (broad d, J=7.9 Hz, 1H), 7.94 (d, J=8.9 Hz, 1H), 7.75 (broad d, J=7.9 Hz, 1H), 7.52 (t, J=7.9 Hz, 1H), 7.05–7.03 (m, 2H), 3.00 (t, J=7.1 Hz, 2H), 1.63 (quint., J=7.1 Hz, 2H), 1.36–1.28 (m, 4H), 0.88 (t, J=6.7 Hz, 3H); MS (ESI) m/z 368/370 (MNa)$^+$; Anal. Calcd for $C_{19}H_{20}NO_3Cl$: C, 64.26; H, 5.07; N, 4.41. Found: C, 64.12; H, 4.74; N, 4.33.

Example 3

Ethyl α-butyl-3-{(4chloro2-hydroxybenzoyl)amino}-β-oxobenzenepropanoate (1: $R_1$=OH, $R_2$, $R_4$ and $R_5$=H, $R_3$=Cl and R=CH(C(O)OEt)(CH$_2$)$_3$Me)

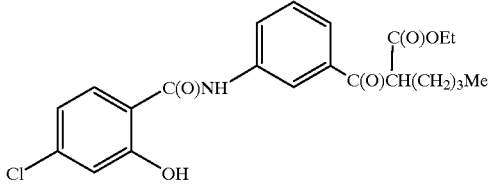

(a) Ethyl α-(2-butenyl)-3-nitro-β-oxobenzenepropanoate

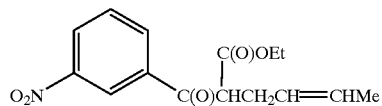

A 60% dispersion of NaH in mineral oil (917 mg, 22.9 mmol) was added over 20 min to a solution of ethyl 3-nitro-β-oxobenzenepropanoate (5.00 g, 21.1 mmol) in THF (50 mL) at such a rate to maintain a gentle reflux. The mixture was stirred at 25° for 30 min and a solution of crotyl bromide (2.95 g, 21.9 mmol) in THF (15 mL) was added over 50 min. The reaction mixture was stirred at 25° for 45 min and then heated at reflux for 16 h. Hexane (100 mL) was added to the cooled mixture. The resulting suspension was filtered and the filtrate was concentrated under reduced pressure. The residue was dissolved in EtOAc and the resulting solution was washed with aqueous 10% citric acid (2×), aqueous saturated $NaHCO_3$ (2×) and brine then was dried ($MgSO_4$) and concentrated under reduced pressure. The residue was purified by flash chromatography (40–63μ silica gel, hexane:EtOAc, 9:1) to afford ethyl α-(2-butenyl)-3-nitro-β-oxobenzenepropanoate (4.60 g, 75% yield):

$^1$H NMR (CDCl$_3$) δ 8.83 (dd, J=2.2, 1.2 Hz, 1H), 8.46 (ddd, J=7.9, 2.2, 1.2 Hz, 1H), 8.31 (dt, J=7.9, 1.2 Hz, 1H), 7.70 (t, J=7.9 Hz, 1H), 5.61–5.52 (m, 1H), 5.39–5.37 (m, 1H), 4.35 (t, J=7.2 Hz, 1H), 4.17, 4.14 (2q, J=7.0, 7.0 Hz, 2H), 2.77 (broad t, J=7.2 Hz, 2H), 1.62 (dd, J=6.4, 1.3 Hz, 3H), 1.19 (t, J=7.0 Hz, 3H).

(b) Ethyl α-aminoct-butyl-β-oxobenzenepropanoate.

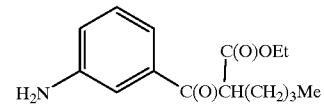

A solution of ethyl α-(2-butenyl)-3-nitro-β-oxobenzenepropanoate (411 mg, 1.41 mmol) in 1,4-dioxane (12 mL) was stirred at 25° for 8.5 h under a hydrogen atmosphere (1 atm) in presence of Pd/BaSO$_4$ (225 mg+150 mg added after 5.5 h). The suspension was filtered (50μ filter) and the filtrate was concentrated under reduced pressure. The residue was purified by flash chromatography (40–63μ silica gel, hexane:EtOAc, 3:1) to give ethyl 3-amino-α-butyl-β-oxobenzenepropionate (242 mg, 65% yield):

$^1$H NMR (CDCl$_3$) δ 7.31 (broad d, J=7.3 Hz, 1H), 7.27–7.23 (m, 3H), 6.88 (broad d, J=7.3 Hz, 1H), 4.22 (t, J=7.2 Hz, 1H), 4.15, 4.14 (2q, J=6.7, 6.7 Hz, 2H), 3.81 (broad s, 2H), 2.02–1.94 (m, 2H), 1.41–1.30 (m, 4H), 1.18 (t, J=7.0 Hz, 3H), 0.89 (t, J=6.7 Hz, 3H).

(c) Ethyl α-butyl-3{(4-chloro-2-hydroxybenzoyl)amino}-β-oxobenzenepropanoate (the title compound of formula 1 of this example)

A solution of 4-chlorosalicylic acid (109 mg, 0.63 mmol) and oxalyl chloride (175 mg, 1.38 mmol) and DMF (50 μL) in CH$_2$Cl$_2$ (5.0 mL) was stirred at 25° for 1 h. The mixture was concentrated under reduced pressure. The residue was dissolved in CH$_2$Cl$_2$ (3.0 mL). A solution of ethyl 3-amino-α-butyl-β-oxobenzenepropanoate (133 mg, 0.51 mmol) in CH$_2$Cl$_2$ (5.0 mL) was added followed by Et$_3$N (152 mg, 1.51 mmol). The reaction mixture was stirred at 25° for 20 h. The mixture was concentrated under reduced pressure and the residue was dissolved in EtOAc. The resulting solution was washed with aqueous saturated NaHCO$_3$ (2×) and brine, then dried (MgSO$_4$), filtered and concentrated under reduced pressure. The residue was purified by flash chromatography (40–63μ silica gel, hexane:EtOAc, 4:1) to give the title compound of this example (100 mg, 48% yield) as a white solid: mp 83–88°;

$^1$H NMR (CDCl$_3$) δ; 12.00 (broad s, 1H), 8.50 (s, 1H), 8.11 (t, J=1.4 Hz, 1H), 7.96 (dd, J=7.9, 1.4 Hz, 1H), 7.77 (dd, J=8.6 Hz, 1H), 7.48 (t, J=7.9 Hz, 1H), 7.03 (d, J=2.0 Hz, 1H), 6.87 (dd, J=8.6, 2.0 Hz, 1H), 4.28 (t, J=7.1 Hz, 1H), 4.15 (q, J=7.0 Hz, 2H), 2.02–1.94 (m, 2H), 1.36–1.28 (m, 4H), 1.18 (t, J=7.0 Hz, 3H), 0.88 (t, J=7.0 Hz, 3H); MS (ESI) 418/420 (MH)$^+$.

Example 4

4-Chloro-2-hydroxy-N-{3-(1-oxohexyl)phenyl}benzamide.

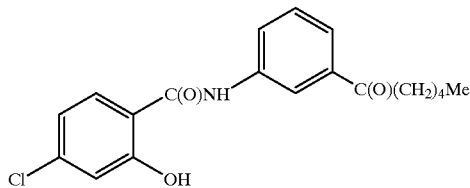

A solution of ethyl α-butyl-3-[(4-chloro-2-hydroxybenzoyl)amino]-β-oxobenzenepropanoate (32.0 mg, 77.0 μmol) and LiOH.H$_2$O (11.0 mg, 0.26 mmol) in THF (3.0 mL) and water (1.5 mL) was heated to 55° for 48 h. The mixture was partitioned between water and EtOAc. The aqueous layer was acidified with aqueous 10% citric acid then extracted with EtOAc. The combined organic layers were dried (MgSO$_4$), filtered and concentrated under reduced pressure. The residue was purified by reversed phase HPLC (Whatman Partisil® ODS-3 C$_{18}$ 10μ, 22×500 mm; 0 to 80% MeCN+0.06% TFA/water+0.06% TFA) to give the title compound (16.0 mg, 60% yield) as a white solid: mp 134–136°; identical to the product of example 2.

Example 5

The following two assays (i and ii) were used to evaluate antiherpes activity.

i) HSV-1 Helicase-primase DNA Primase Assay

The HSV-1 helicase-primase enzyme used for primase assays was expressed and isolated as described (M. S. Dodson et al., *J. Biol. Chem.* 1989, 264, 20835; S. Dracheva et al. *J. Biol. Chem.* 1995, 270, 14148) except that the UL5-expressing baculovirus was changed to express UL5 (K103A). The resulting altered enzyme contained no detectable helicase, DNA-dependent ATPase, or ATPase activity. However, DNA primase activity was increased over the wild type enzyme.

Assay: DNA primase activity was measured by the incorporation of [$^3$H]GTP into newly synthesized primers by the UL5(K103A) helicase-primase holoenzyme. Assays were performed using as template the 50-mer single-stranded DNA oligonucleotide 5'-CTTCTTCGGT TCCGACTAC CCCTCCCGAC TGCCTATGAT GTTTATCCTT T G-3'OH (SEQ ID No. 1) derived from the preferred priming site on φX174 single-stranded DNA [D. J. Teney et al., *J. Biol. Chem.* 1995, 270, 9129–9136]. The reaction mixtures (60 μl) contained 20 μM Tris-HCl pH 8.0, 5 mM magnesium chloride, 1 mM DTT, 0.01 % CHAPS, 100 μM each of ATP, GTP, CTP, 10 μM [biotin]UTP, 1 μCi [$^3$H]GTP (specific activity 30.8 Ci/mmol), 1 μg of the 50-mer template and 45 μg/ml of the UL5(K103A)-altered helicase-primase holoenzyme. The samples were incubated at 34° for 45 min in a circulating waterbath and reactions were quenched by the addition of 20 μl 0.5 M EDTA pH 8. Then, 50 μl of the reaction mixtures were transferred to Millipore filtration plates (MHVB N45, 0.45 μm) containing 40 μl of immobilized avidin beads (Pierce). After incubating 30 min at room temperature on a microplate shaker, the wells were washed five times with 300 μl wash buffer (50 mM 4-(2-hydroxyethyl)-1-piperazineethanesulfonic acid (HEPES) pH 7.5 and 0.5 M NaCl) and the filter plates were aspirated to dryness. The radioactivity in each well was counted using the Topcount® after adding 100 μl Microscint® 20 (Camberra-Packard Canada, Mississauga, Ontario, Canada) to each well.

IC$_{50}$ DETERMINATIONS

In all cases, compounds were tested in three-fold serial dilutions and the results were expressed as percent inhibition as compared to control reactions without inhibitor. IC$_{50}$ (i.e., inhibitor concentration that yielded 50% inhibition of enzyme activity) values were determined from dose-response curves using SAS software (SAS Institute, Cary, N.C., USA). A non-linear regression analysis based on the Hill equation, M. Dixon and E.C. Webb Enzymes, Academic Press: New York, N.Y., USA, 1979, was applied to the percent inhibition-concentration data.

ii) Inhibition of Herpes Simplex Virus (HSV-1) Replication in Cell Culture

Assay: BHK-21 cells clone 13 (ATCC CCL10) were incubated for two days in 850 cm$^2$ roller bottles (2×10$^7$ cells/bottle) with α-MEM medium (Gibco Canada Inc., Burlington, Ontario, Canada) supplemented with 8% (v/v) fetal bovine serum (FBS, Gibco Canada, Inc.). The cells were trypsinized and then 3,000 cells in 100 μL of fresh medium were transferred into each well of a 96-well microtiter plate. The cells were incubated at 37° for a period of 3 days to reach a density of 50,000 cells per well. The cells were washed twice with 100 μL of α-MEM supplemented with 2% heat inactivated FBS and incubated for 1–2 h in 100 μL of the same medium.

Thereafter, the cells were infected with HSV-1 strain F or KOS (multiplicity of infection=0.05 PFU/cell) in 50 μL of α-MEM supplemented with 2% heat inactivated FBS. Following one hour of virus absorption at 37°, the medium was removed and the cells were washed with α-MEM supplemented with 2% heat inactivated FBS (2×100 μL). The cells were incubated with or without 100 μL of the appropriate concentration of test reagent in α-MEM medium supplemented with 2% heat inactivated FBS. After 24 h of incubation at 37°, the extent of viral replication was determined by an ELISA assay; for instance, the following assay that detects the late glycoprotein C of HSV-1.

Cells were fixed in the microtiter plate with 100 μL of 0.063% glutaraldehyde in phosphate buffered saline for 30 min at room temperature. The microtiter plate was then washed once with casein blocking solution and blocked with 200 μL of the same solution for 1 h at room temperature. Thereafter, 100 μL of mAb C11 recognizing the glycoprotein C of HSV-1 (see E. Trybala et al., Journal of General Virology, 1994, 75, 743) was added to each well for 2 h at room temperature. The plate was washed three times with phosphate buffered saline containing 0.05% polyoxyethylene (20) sorbitan monooleate. The cells were incubated with 100 μL of sheep anti-mouse IgG horseradish peroxidase for 1 h at room temperature in the dark.

The plate was washed three times with 200 μL of the above-noted phosphate buffer saline preparation, and then once with 0.1 M sodium citrate (pH 4.5). Thereafter, 100 μL of orthophenylenediamine dihydrochloride (OPD, Gibco, Canada Inc.) was added to each well. The plate was agitated on a microplate shaker for 30 min in the dark. Color development was monitored at 450 nm using a microplate spectrophotometer.

SAS was used to calculate % inhibition of viral replication and to generate $EC_{50}$ values.

The results from assays i and ii for compounds are noted in TABLE 3. Results for assay i are expressed under the heading HSV-1, $IC_{50}$ (μM). Results for assay ii are expressed under the heading HSV-1, $EC_{50}$ (μM). In both instances category "A" includes compounds having an $IC_{50}$ or an $EC_{50}$ of less than about 1 μM; category "B" includes compounds having an $IC_{50}$ or an $EC_{50}$ falling within the range of about 1–100 μM; and category "C" includes compounds having an $IC_{50}$ or an $EC_{50}$ of greater than about 100μM.

TABLE 1

Compound of formula 1 having the structure

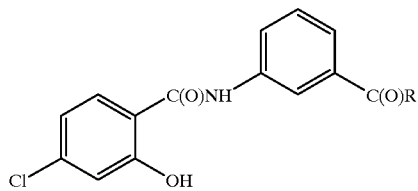

| BILS # | Entry No. | R | ESI/MS (m/z) $(M + H)^+$, unless noted otherwise, and isotopic peak due to chlorine | HPLC[1] Purity (%) |
|---|---|---|---|---|
| 867 | 1 | CH(C(O)OEt)(CH$_2$)$_3$Me | 418/410 | 93.3 |
| 868 | 2 | Me | 290/292 | 97.4 |
| 872 | 3 | CH$_2$C(O)OEt | 362/364 | 87 (7% enol) |
| 883 | 4 | (CH$_2$)$_2$Me | 340/342* | 99.5 |
| 884 | 5 | CH$_2$Ph | 364/366** | 98.4 |
| 885 | 6 | —⬡ (cyclohexyl) | 356/358** | 99.9 |
| 893 | 7 | CH$_2$CH$_2$Ph | 378/380** | 97.3 |
| 886 | 8 | OCH$_2$-(2-pyridyl) | 381/383** | 98.2 |
| 901 | 9 | OCH$_2$Ph | 380/382** | 99 |
| 878 | 10 | piperidinyl | 381/383* | 99.7 |
| 879 | 11 | N(Me)CH$_2$CH$_2$-(2-pyridyl) | 410/412 | 99.7 |
| 880 | 12 | N(Me)(CH$_2$)$_3$Me | 361/363 | 99.6 |

TABLE 1-continued
Compound of formula 1 having the structure
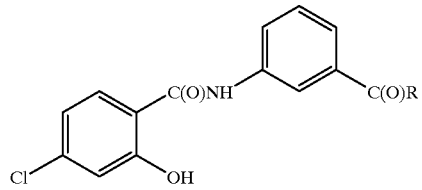
| BILS # | Entry No. | R | ESI/MS (m/z) (M + H)+, unless noted otherwise, and isotopic peak due to chlorine | HPLC[1] Purity (%) |
|---|---|---|---|---|
| 888 | 13 | 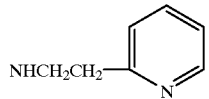 | 409/411* | 100 |
| 889 | 14 | 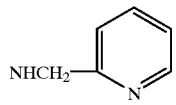 | 396/398 | 98.1 |
| 890 | 15 | NHCH₂Ph | 403/405* | 93.7 |
| 877 | 16 | NH(CH₂)₃Me | 369/371* | 99.4 |
| 881 | 17 | 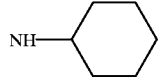 | 382/384 | 100 |
| 882 | 18 | NH—cyclohexyl | 395/397* | 97.1 |
| 892 | 19 | 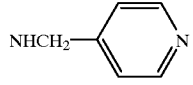 | 380/382** | 99.8 |
[1]HPLC conditions: Vydac ®, C₁₈,5μ, 15 cm; solvent: 5–100% MeCN + 0.06% TFA/H₂O + 0.06% TFA in 25 min; UV detector: 230 nm
*(M + Na)+
**(M − H)−

TABLE 2

Compound of formula 1 having the structure

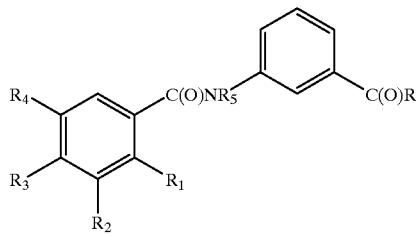

| BILS # | Entry No. | $R_1$ | $R_2$ | $R_3$ | $R_4$ | $R_5$ | R | ESI/MS (m/z) $(M + H)^+$, unless noted otherwise, and if present isotopic peak due to chlorine | HPLC[1] Purity (%) |
|---|---|---|---|---|---|---|---|---|---|
| 876 | 101 | OH | Cl | H | H | H | $(CH_2)_4Me$ | 344/346** | 97.2 |
| 895 | 102 | OH | H | Me | H | H | $NHCH_2Ph$ | 359/361** | 97.5 |
| 896 | 103 | OH | H | OMe | H | H | $NHCH_2Ph$ | 375/377** | 96.8 |
| 897 | 104 | OH | H | $N_3$ | H | H | $NHCH_2Ph$ | 386** | 99.2 |
| 898 | 105 | $NH_2$ | H | H | H | H | $NHCH_2Ph$ | 346 | 95.8 |
| 899 | 106 | OH | H | $N_3$ | I | H | $NHCH_2Ph$ | 514 | 100 |
| 902 | 107 | $NH_2$ | H | Cl | H | H | $NHCH_2Ph$ | 380/382 | 95.8 |
| 903 | 108 | OH | H | $NH_2$ | H | H | $NHCH_2Ph$ | 362/364 | 95.0 |
| MEN 2161 | 109 | OH | H | Cl | H | H | $NHCH_2Ph$ | 368/370* | 98.7 |
| MEN 2163 | 110 | OH | H | H | Cl | H | $NHCH_2Ph$ | 346/348 | 100.0 |
| MEN 1941 | 111 | OH | H | H | H | H | $NHCH_2Ph$ | 311 | 99.0 |
| MEN 2141 | 112 | OH | H | OH | H | H | $NHCH_2Ph$ | 328 | 100.0 |
| 887 | 113 | OH | H | H | H | Me | $NHCH_2Ph$ | 358/360** | 98.2 |

[1]HPLC conditions: Vydac ®, $C_{18}$ 5$\mu$ 15 cm; solvent: 5–100% MeCN + 0.06% TFA/$H_2O$ + 0.06% TFA in 25 min; UV detector: 230 nm
*$(M + Na)^+$
**$(M - H)^-$

TABLE 3

Enzyme inhibition and cell culture data of compounds in Tables 1 and 2

| Compound Entry No. | HSV-1 $IC_{50}$ ($\mu M$) | HSV-1 $EC_{50}$ ($\mu M$) |
|---|---|---|
| 1 | B | B |
| 2 | B | B |
| 3 | B | B |
| 4 | B | B |
| 5 | B | B |
| 6 | B | B |
| 7 | B | — |
| 8 | A | B |
| 9 | A | — |
| 10 | C | >A |
| 11 | C | |
| 12 | C | >A |
| 13 | A | B |
| 14 | B | B |
| 15 | A | B |
| 16 | B | B |
| 17 | A | B |
| 18 | B | >A |
| 19 | B | — |
| 101 | B | B |
| 102 | A | — |
| 103 | A | — |
| 104 | A | — |
| 105 | C | — |
| 106 | A | — |
| 107 | C | — |
| 108 | B | — |
| 109 | B | — |
| 110 | B | B |
| 111 | B | B |
| 112 | C | — |
| 113 | C | — |
| 114 | B | — |

What is claimed is:

1. A compound of formula 1

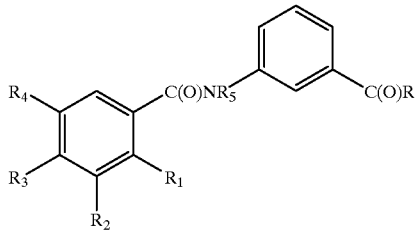

(1)

wherein
$R_1$ is hydroxy or amino;
$R_2$ is hydrogen, halo, $(C_{1-4})$alkyl or $(C_{1-4})$alkoxy;
$R_3$ is halo, amino or azido;
$R_4$ has the same significance as $R_2$;
$R_5$ is hydrogen or $(C_{1-4})$alkyl; and
R is $(C_{1-7})$alkyl, $(C_{3-6})$cycloalkyl, {phenyl$(C_{1-7})$alky}, {phenyl$(C_{1-7})$alkoxy}, {{(monocyclic heterocyclo)-{$(C_{1-7})$alkoxy}}, CH(W)C(O){O-$(C_{1-4})$alkyl} wherein W is hydrogen or $(C_{1-7})$alkyl, or

wherein Y in hydrogen or $(C_{1-7})$alkyl, and Z is $(C_{1-7})$alkyl, $(C_{3-6})$cycloalkyl, {$(C_{3-6})$cycloalkyl}-{$(C_{1-7})$alkyl}, phenyl$(C_{1-7})$alkyl or {{(monocyclic heterocyclo)-{$(C_{1-7})$alkyl}}, or Y and Z together with the nitrogen atom to which they are attached represent, 1-pyrrolidinyl, 1-piperidinyl, 4-morpholinyl or 1-(4-methylpiperazinyl);
with the provisos that (1) when R is CH(W)C(O)-{O-$(C_{1-4})$alkyl} as defined herein, then $R_5$ is hydrogen; and (2) at least one of $R_2$, $R_3$ and $R_4$ is other than hydrogen; or a salt thereof.

2. A compound according to claim 1, wherein $R_1$ is hydroxy.

3. A compound according to claim 1, wherein $R_2$ is hydrogen or halo.

4. A compound according to claim 1, wherein $R_2$ is hydrogen or chloro.

5. A compound according to claim 1, wherein $R_2$ is hydrogen.

6. A compound according to claim 1, wherein $R_3$ is chloro, amino or azido.

7. A compound according to claim 1, wherein $R_3$ is amino or azido.

8. A compound according to claim 1, wherein $R_4$ is hydrogen or halo.

9. A compound according to claim 1, wherein $R_4$ is hydrogen, chloro or iodo.

10. A compound according to claim 1, wherein $R_5$ is hydrogen or methyl.

11. A compound according to claim 1, wherein $R_5$ is hydrogen.

12. A compound according to claim 1, wherein R is methyl, ethyl, propyl, butyl, pentyl, hexyl, cyclopentyl, cyclohexyl, phenylmethyl, 2-phenylethyl, phenylmethoxy, 2-phenylethoxy, 2-, 3- or 4pyridinylmethoxy, 2-(2-, 3- or 4-pyridinyl)ethoxy, $CH_2C(O)\{O-\{(C_{1-4})alkyl\}\}$, $CH\{(C_{1-7})alkyl\}C(O)\{OC_{1-4}alkyl\}$, $(C_{1-7})alkylamino$, cyclopentylamino, cyclohexylamino, (cyclohexylmethyl)amino, (2-cyclohexylethyl)amino, (phenylmethyl)amino, (2-phenylethyl)amino, 2-(3- or (4-pyridylmethyl)amino or 2-(2-, (3- or (4-pyridylethyl)amino.

13. A compound according to claim 1 wherein R is pentyl, hexyl, cyclohexyl, phenylmethyl, 2-phenylethyl, phenylmethoxy, 2-, 3- or 4-pyridinylmethoxy, $CH_2C(O)OCH_2CH_3$, $CH(CH_2CH_2CH_2CH_3)C(O)OCH_2CH_3$, ethylamino, propylamino, butylamino, cyclohexylamino, (cyclohexylmethyl)-amino, (2-cyclohexylethyl)amino, (phenylmethyl)amino, (2-phenylethyl)amino, or (2-, (3- or (4-pyridylmethyl)amino, or 2-(2-, (3-, or (4-pyridinylethyl) amino.

14. A pharmaceutical composition for the treatment or prevention of a disease or condition involving herpes virus, comprising an effective amount of a compound according to claim 1, and a pharmaceutically acceptable carrier or auxiliary agent.

15. A method for treating a herpes virus infection in a mammal comprising administering to the mammal a therapeutically effective amount of a compound according to claim 1.

16. A method for treating a herpes virus infection in a mammal, comprising administering to the mammal a compound according to claim 1, in conjunction with an additional antiviral agent.

17. The method of claim 16, wherein the additional antiviral agent is selected from acyclovir, pencyclovir, famciclovir, valaciclovir and ganciclovir.
18. A method for inhibiting herpes virus replication, comprising exposing cells infected with herpes virus to a compound according to claim 1.
19. A compound selected from
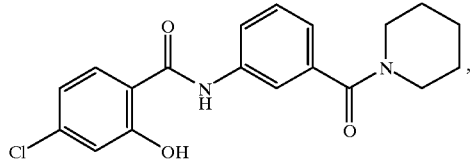
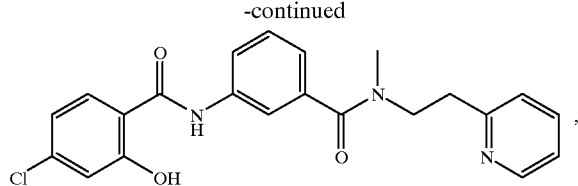
and
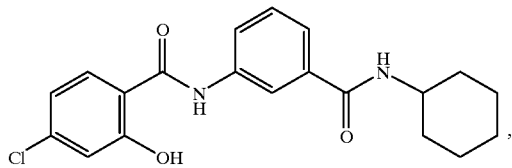
or a salt thereof.
* * * * *